(12) United States Patent
Schultz (10) Patent No.: US 8,672,904 B1
(45) Date of Patent: Mar. 18, 2014

(54) SPLASH SHIELD SYSTEMS

(76) Inventor: Joseph P. Schultz, Atlanta, GA (US)

( * ) Notice: Subject to any disclaimer, the term of this patent is extended or adjusted under 35 U.S.C. 154(b) by 783 days.

(21) Appl. No.: 12/714,316

(22) Filed: Feb. 26, 2010

Related U.S. Application Data (60) Provisional application No. 61/231,638, filed on Aug. 5, 2009.

(51) Int. Cl.
*A61H 33/04* (2006.01)

(52) U.S. Cl.
USPC ........... 604/302; 604/118; 604/294; 604/295; 604/300; 604/301; 222/386; 222/541.9

(58) Field of Classification Search
USPC .................. 604/294, 295, 300, 301, 302, 118
See application file for complete search history.

(56) References Cited

U.S. PATENT DOCUMENTS

| | | | |
|---|---|---|---|
| 2,920,624 A * | 1/1960 | Lerner et al. | 604/301 |
| 4,740,206 A | 4/1988 | Allander | |
| 4,798,599 A | 1/1989 | Thomas | |
| 4,834,728 A | 5/1989 | McKenna | |
| 5,030,214 A * | 7/1991 | Spector | 604/301 |
| 5,224,940 A | 7/1993 | Dann | |
| 5,496,290 A * | 3/1996 | Ackerman | 604/268 |
| 5,607,410 A | 3/1997 | Branch | |
| 5,611,788 A | 3/1997 | Marchment | |
| 6,468,253 B1 | 10/2002 | Rucinski | |
| 6,540,726 B1 | 4/2003 | Follman et al. | |
| 6,858,020 B2 * | 2/2005 | Rusnak | 604/131 |
| 7,621,897 B1 | 11/2009 | Berke | |
| 2008/0255527 A1 | 10/2008 | Osborne | |

* cited by examiner

*Primary Examiner* — Tatyana Zalukaeva
*Assistant Examiner* — Ilya Treyger
(74) *Attorney, Agent, or Firm* — Stoneman Law Patent Group; Martin L. Stoneman (57) ABSTRACT

A medical system comprising apparatus and methods for improved irrigation and lavage in wound management. The device attaches to at least one irrigation fluid source and is configured to administer the fluid indirectly to a wound or tissue.

44 Claims, 5 Drawing Sheets

FIG. 14

SPLASH SHIELD SYSTEMS

CROSS-REFERENCE TO RELATED APPLICATION

The present application is related to and claims priority from prior provisional application Ser. No. 61/231,638, filed Aug. 5, 2009, entitled "SPLASH SHIELD SYSTEMS", the content of which is incorporated herein by this reference and is not admitted to be prior art with respect to the present invention by the mention in this cross-reference section.

BACKGROUND

This invention relates to providing a medical system assisting more efficient and safer performance of medical procedures. More particularly, this invention concerns a medical system comprising apparatus and methods for improved irrigation and lavage in wound management. With respect to medical irrigation procedures, when a patient presents with a wound, it is often desirable to initially irrigate the wound using a cleansing solution, such as normal saline. Irrigation in wound management has the beneficial effect of purging foreign bacteria, debris, and/or chemicals from damaged tissues of the wound bed, to diminish the potential of infection and other complications. When using large volumes of fluid, there is an increased likelihood for the contamination of adjacent tissues and surfaces, splashing of biological and chemical contaminants onto a health care provider, and/or drenching the patient with fluid. This is undesirable as the risk of spreading of disease is heightened and there are undesirable effects associated with excessive wetting of a patient (for example, trauma patients with multiple wounds might become hypothermic from large amounts of irrigation fluid evaporating on their bodies). These inherent disadvantages may decrease the incentive for a caregiver, such as a physician, to use optimal volumes of irrigation fluid; and therefore increasing the risk of later complications.

The time necessary to prepare the irrigation and lavage procedures can also directly impinge on patient care. The use of overly complex irrigation apparatus typically results in delays to treatment, especially when preparation of such apparatus requires assembly and manipulation of multiple elements. The most commonly used conventional devices in ocular irrigation are difficult to place, painful, and not tolerated well by most patients. Conventional ocular devices are difficult to place in children, who are often frightened by the direct eye contact required by such devices. Conventional devices are difficult to place in field, require anesthetic drops, takes a lot of precious time to set up while injury (e.g., a chemical splash injury) continues to damage eye tissues. Furthermore, conventional ocular devices require training to administer properly, can cause eye injury if not used properly, and are not appropriate for washing out particulate contamination as the device may grind the particulates against the cornea.

Conversely, improvised puncturing of fluid bottles, as sometimes performed by emergency care clinicians, provides little or no spray control or protection from splashing and secondary contamination; and such improvised puncturing of fluid bottles increases the risk of a needle-stick injury. In addition, conventional irrigation and lavage procedures can sometimes cause additional trauma in delicate tissues if the fluid is applied forcefully and directly on the wound.

OBJECTS AND FEATURES OF THE INVENTION

A primary object and feature of the present invention is to fulfill the above-mentioned needs by the provision of an improved splash shield system. A further primary object and feature of this invention is to provide a splash shield system which provides an indirectly applied "flooding" of irrigation fluid to a wound environment. Another primary object and feature of this invention is to provide a splash shield system which easily accommodates connection to a variety of different sources of irrigation fluid, including fluid supplied from standard saline bottles. Another primary object and feature of the present invention is to provide such a splash shield system which supplies a relatively constant but continuously exchanging volume of irrigation fluid to the wound. A further primary object and feature of the present invention is to provide such a system that is efficient, inexpensive, and handy. Other objects and features of this invention will become apparent with reference to the following descriptions.

SUMMARY OF THE INVENTION

In accordance with a preferred embodiment hereof, this invention provides a medical system relating to medical procedures involving fluid irrigation of tissues comprising: at least one sprayer configured to produce at least one spray of fluid to bathe at least one target tissue; substantially surrounding such at least one sprayer, at least one splash shield structured and arranged to limit splashing of the fluid during production of the at least one spray; and at least one fluid conduit structured and arranged to conduct the fluid between at least one source of the fluid and such at least one sprayer; wherein such at least one sprayer comprise at least one spray director structured and arranged to direct the at least one spray of the fluid generally toward at least one inside surface of such at least one splash shield; and wherein the fluid is delivered substantially indirectly to the at least one target tissue. Moreover, it provides such a medical system wherein such at least one splash shield further comprises at least one anatomical engager configured engage at least one anatomical structure surrounding the at least one target tissue during production of the at least one spray.

Additionally, it provides such a medical system wherein such at least one splash shield further comprises at least one fluid retainer configured to retain, when such at least one anatomical engager is engaged with the at least one anatomical structure, at least one administered volume of the fluid in physical contact with the at least one target tissue. Also, it provides such a medical system further comprising at least one releasable coupler structured and arranged to releasably couple such at least one fluid conduit to at least one source of the fluid. In addition, it provides such a medical system wherein such at least one releasable coupler comprises at least one threaded coupler structured and arranged to threadably engage at least one bottle-type container containing the fluid. And, it provides such a medical system wherein such at least one releasable coupler further comprises at least one syringe receiver structured and arranged to receive at least one syringe usable to dispense the fluid into such at least one fluid conduit. Even further, it provides such a medical system wherein such at least one syringe receiver is structured and arranged to receive at least one Luer-type connector of the at least one syringe. Further, it provides such a medical system wherein said at least one releasable coupler comprises at least one Luer-type connector receiver structured and arranged to receive at least one Luer-type connector of the at least one source of the fluid. Further, it provides such a medical system wherein such at least one releasable coupler is structured and arranged to couple with at least one standard wide-mouth standard irrigation pour bottle containing the fluid.

Even further, it provides such a medical system wherein such at least one releasable coupler further comprises at least one fluid seal structured and arranged to form at least one fluid-resistant seal between the at least one standard wide-mouth pour bottle and such at least one releasable coupler. Further, it provides such a medical system wherein such seal is adapted to seal on at least one standard wide mouth standard irrigation bottle. Furthermore, it provides such a medical system wherein such seal is adapted to seal on at least three commercially-available wide mouth standard irrigation bottles comprising slightly differing bottle end opening configurations. Further, it provides such a medical system wherein such seal is adapted to seal on at least three commercially-available wide mouth standard irrigation bottles at least produced by Baxter Healthcare Corporation of Deerfield Ill., Hospira Worldwide Inc. of Lake Forest Ill., and B. Braun Medical Inc. of Allentown Pa.

Moreover, it provides such a medical system wherein such at least one fluid retainer comprises: at least one outer wall configured to form at least one closed curve continuously surrounding the at least one target tissue; wherein such at least one outer wall comprises such at least one anatomical engager; wherein, when engaged on the at least one anatomical structure surrounding the at least one target tissue, such at least one splash shield comprises at least one fluid-holding chamber structured and arranged to hold the at least one administered volume of the fluid in physical contact with the at least one target tissue.

Additionally, it provides such a medical system wherein: such at least one anatomical engager comprises at least one shape conformer structured and arranged to generally conform to the surface topography of the at least one anatomical structure surrounding the at least one target tissue; and such at least one shape conformer is configured to assist in the formation of at least one fluid-retaining seal between such at least one anatomical engager and the at least one anatomical structure to retain the at least one administered volume of the fluid in physical contact with the at least one target tissue. Further, it provides such a medical system wherein the preferred means of administration, by pooling within such at least one fluid-holding chamber the fluid adjacent the eye, suppresses the patient's blinking reflex; wherein, the system permits deeper penetration under areas that would otherwise covered by anatomical structures of the closed eye (eyelids).

Also, it provides such a medical system wherein such at least one anatomical engager comprises at least one resilient material. In addition, it provides such a medical system wherein the at least one closed curve of such at least one outer wall comprises at least one substantially circular-shaped section.

And, it provides such a medical system wherein such at least one outer wall further comprises: extending through such at least one outer wall, at least one drainage passage structured and arranged to drain the fluid from within such at least one fluid-holding chamber; wherein such at least one drainage passage comprises in fluid communication with such at least one fluid-holding chamber, at least one drainage inlet, and at least one discharge outlet configured to discharge the fluid entering such at least one drainage inlet externally of such at least one outer wall. Further, it provides such a medical system wherein such at least one drainage passage is configured to retain at least one minimum administered volume of the fluid within such at least one fluid-holding chamber and drain, from such at least one fluid-holding chamber, amounts of the fluid in excess of the at least one minimum administered volume. Even further, it provides such a medical system wherein: such at least one discharge outlet is situated in closer proximity to such at least one anatomical engager than such at least one drainage inlet; and wherein such at least one drainage inlet and such at least one discharge outlet comprise, within such at least one outer wall, differing vertical elevations when such at least one anatomical engager is oriented in a downward contact orientation.

Moreover, it provides such a medical system wherein such at least one splash shield further comprises at least one transparent portion configured to provide a view of the at least one target tissue from outside such at least one splash shield, even when such at least one anatomical engager is engaging the at least one anatomical structure surrounding the at least one target tissue. Additionally, it provides such a medical system wherein such at least one sprayer, such at least one splash shield and such at least one coupler comprise a single monolithically-molded polymer.

Also, it provides such a medical system further comprising: at least one bottle containing the fluid; wherein such at least one at least one bottle is operably compatible with such at least one coupler. In addition, it provides such a medical system wherein: such at least one anatomical engager comprises at least one facial engager structured and arranged to engage periorbital facial structures surrounding at least one eye; such at least one shape conformer is structured and arranged to conform closely to the topography of the periorbital facial structures surrounding at least one eye; and such at least one shape conformer is configured to assist in the formation of at least one fluid-retaining seal between such at least one anatomical engager and the periorbital facial structures surrounding at least one eye to retain the at least one administered volume of the fluid in physical contact with the at least one eye. And, it provides such a medical system wherein such at least one shape conformer comprises at least one saddle-shaped anatomical engager.

Further, it provides such a medical system wherein such at least one discharge outlet is positioned within such at least one outer wall to discharge laterally of the lateral canthus of the at least one eye when such at least one anatomical engager is engaged to form the at least one fluid-retaining seal with the periorbital facial structures. Even further, it provides such a medical system wherein such at least one discharge outlet is sized to receive at least one Luer-type slip connector.

In accordance with another preferred embodiment hereof, this invention provides a medical system relating to medical procedures involving irrigation of at least one eye comprising: at least one fluid conduit structured and arranged to conduct the fluid; in fluid communication with such at least one fluid conduit at least one sprayer configured to produce at least one spray of the fluid and at least one threaded coupler structured and arranged to threadably couple such at least one sprayer with at least one bottle containing the fluid; and substantially surrounding such at least one sprayer, at least one splash shield structured and arranged to limit splashing of the fluid during production of the at least one spray of the fluid; wherein such at least one splash shield comprises at least one facial-engager configured to engage periorbital facial structures surrounding the at least one eye; wherein such at least one facial-engager comprises at least one shape conformer structured and arranged to conform closely to the topography of the periorbital facial structures surrounding at least one eye; and wherein such at least one shape conformer is configured to assist in the formation of at least one fluid-retaining seal between such at least one facial-engager and the periorbital facial structures to pool at least one administered volume of the fluid in physical contact with the at least one eye.

Moreover, it provides such a medical system wherein: such at least one sprayer comprise at least one spray director structured and arranged to direct the at least one spray of the fluid generally toward at least one inside surface of such at least one splash shield; and the fluid is delivered substantially indirectly to the at least one target tissue. Additionally, it provides such a medical system wherein such at least one splash shield further comprises: at least one outer wall configured to form at least one closed curve continuously surrounding the at least one eye; wherein such at least one outer wall comprises such at least one anatomical engager; and wherein, when engaged on the periorbital facial structures surrounding the at least one eye, such at least one splash shield comprises at least one fluid-holding chamber structured and arranged to hold the at least one administered volume of the fluid in physical contact with the at least one eye. Also, it provides such a medical system wherein such at least one anatomical engager comprises at least one resilient material.

In addition, it provides such a medical system wherein such at least one coupler comprises at least one threaded coupler structured and arranged to threadably engage at least one bottle-type container containing the fluid. And, it provides such a medical system wherein such at least one releasable coupler further comprises at least one syringe receiver structured and arranged to receive at least one syringe usable to dispense the fluid into such at least one fluid conduit. Further, it provides such a medical system wherein such at least one outer wall further comprises: extending through such at least one outer wall, at least one drainage passage structured and arranged to drain the fluid from within such at least one fluid-holding chamber; wherein such at least one drainage passage comprises in fluid communication with such at least one fluid-holding chamber, at least one drainage inlet, and at least one discharge outlet configured to discharge the fluid entering such at least one drainage inlet externally of such at least one outer wall.

Even further, it provides such a medical system wherein such at least one drainage passage is configured to retain at least one minimum administered volume of the fluid within such at least one fluid-holding chamber and drain, from such at least one fluid-holding chamber, amounts of the fluid in excess of the at least one minimum administered volume. Moreover, it provides such a medical system wherein: such at least one discharge outlet is situated in closer proximity to such at least one facial-engager than such at least one drainage inlet; and wherein such at least one drainage inlet and such at least one discharge outlet comprise, within such at least one outer wall, differing vertical elevations when such at least one facial-engager is oriented in a downward contact with the periorbital facial structures.

Additionally, it provides such a medical system wherein such at least one splash shield further comprises at least one transparent portion configured to provide a view of the at least one target tissue from outside such at least one splash shield, even when such at least one facial-engager is engaging the periorbital facial structures surrounding the at least one eye. Also, it provides such a medical system wherein such at least one sprayer, such at least one splash shield and such at least one releasable coupler comprise a single monolithically-molded polymer. In addition, it provides such a medical system further comprising: at least one bottle containing the fluid; wherein such at least one at least one bottle is operably compatible with such at least one coupler. And, it provides such a medical system wherein such at least one discharge outlet is sized to receive at least one Luer-type slip connector. Further, it provides such a medical system further comprising extending into such at least one at least one bottle, at least one fluid transport tube configured to transport the fluid from a bottom portion of such at least one at least one bottle to such at least one fluid conduit.

In accordance with another preferred embodiment hereof, this invention provides a medical system relating to ophthalmologic medical procedures involving fluid irrigation of at least one eye, such system comprising: a hollow cylindrical wall comprising an open proximal end, an open distal end, a proximal interior chamber, a distal interior chamber, and a transverse dividing wall to transversely divide such proximal interior chamber from such distal interior chamber; wherein such open distal end comprises a threaded coupler structured and arranged to assist threaded coupling of such hollow cylindrical wall to a threaded opening of a bottle containing the fluid; wherein such transverse dividing wall comprises, at least one sprayer configured to produce, within such distal interior chamber, at least one directed spray of the fluid discharged into such proximal interior chamber from the bottle containing the fluid; wherein such open distal end comprises at least one facial-engager configured to engage periorbital facial structures of the at least one eye; and wherein the at least one directed spray of the fluid by such at least one sprayer is configured to direct the at least one spray of the fluid toward impingement with an interior surface of such hollow cylindrical wall of such distal interior chamber. Even further, it provides such a medical system wherein such a distal interior chamber is structured and arranged to hold a pool of the fluid, discharged from such at least one sprayer, in contact with the at least one eye.

In accordance with another preferred embodiment hereof, this invention provides a medical system relating to medical procedures involving fluid irrigation procedures comprising: sprayer means for spraying fluid to bathe at least one target; conduit means for conducting the fluid to at least one inside surface of such sprayer means; and splash deterrent means for deterring splashing of the fluid bathing the at least one target; wherein such sprayer means comprises director means for directing the fluid from such sprayer means generally towards at least one inside surface of such splash deterring means. In accordance with another preferred embodiment hereof, this invention provides each and every novel feature, element, combination, step and/or method disclosed or suggested by this patent application.

DETAILED DESCRIPTION OF THE BEST MODES AND PREFERRED EMBODIMENTS OF THE INVENTION

Figures 1, 2, 3:
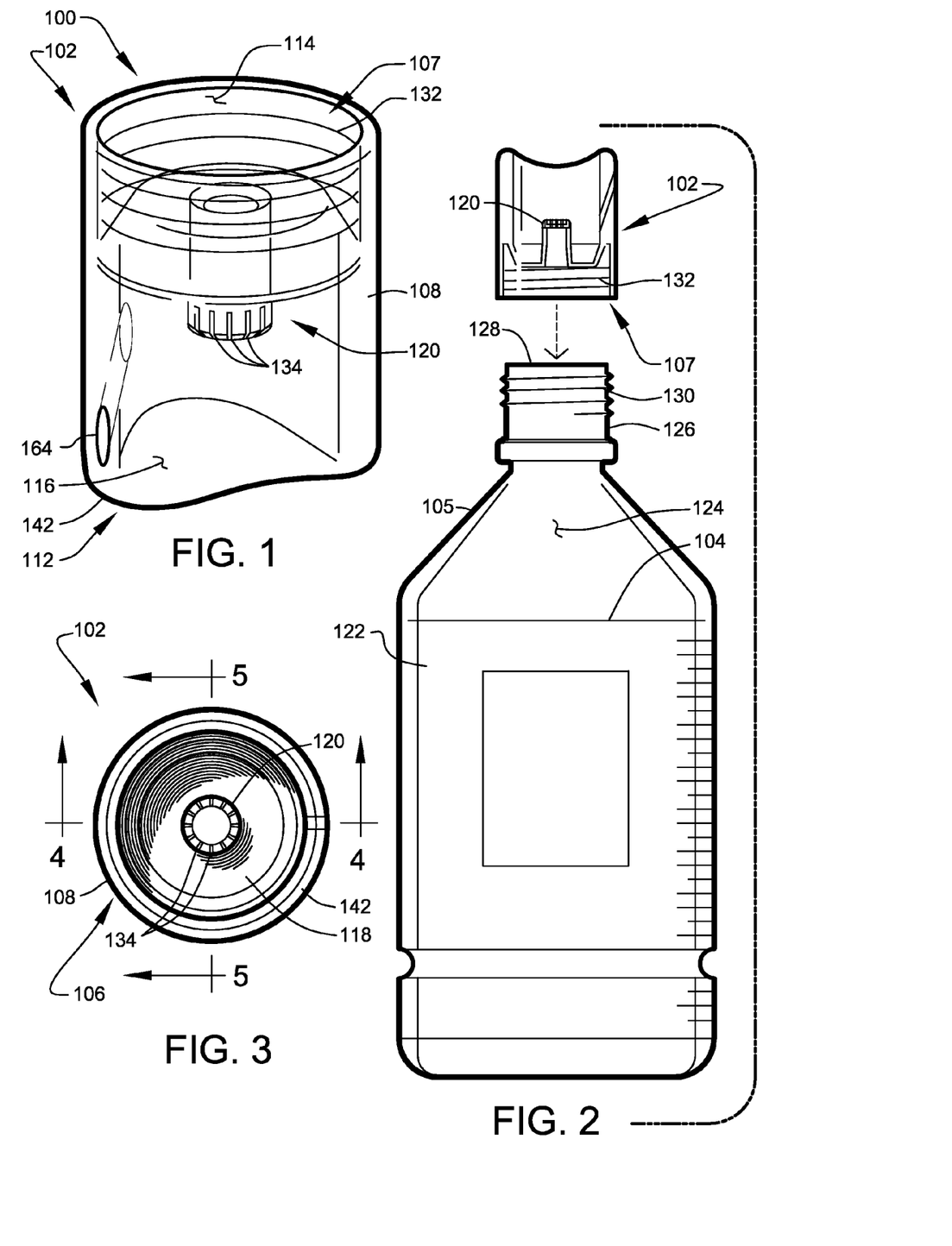
FIG. 1 shows a perspective view, illustrating a splash shield for wound irrigation and similar lavage procedures, according to a preferred embodiment of the present invention.
FIG. 2 shows a side exploded view, illustrating the splash shield of FIG. 1 in axial alignment with a bottle containing fluid useable in wound irrigation, according to another preferred embodiment of the present invention.
FIG. 3 shows a bottom view of the splash shield, according to the preferred embodiment of FIG. 1.

FIG. 1 shows a perspective view, illustrating splash shield 102 for wound irrigation, according to a preferred embodiment of splash shield system 100. FIG. 2 shows a side exploded view, illustrating splash shield 102 in position for attachment on a preferred source of fluid 104 used to irrigate wounds.

Preferred embodiments of splash shield system 100 comprise medical irrigation devices configured to assist safe, convenient, and efficient wound management through controlled fluid irrigation of body tissues. Preferred embodiments of splash shield system 100, preferably including splash shield 102, have specific features designed to provide controlled dispensing of fluid 104 directly from at least one source of irrigation fluid 104. As illustrated in FIG. 2, splash shield 102 preferably comprises at least one releasable coupler 107 preferably configured to releasably couple splash shield 102 to a ready-to-use source of fluid 104, preferably in the form of a hand graspable container, more preferably a bottle, most preferably a standard irrigation fluid bottle 105, as shown.

Preferred irrigation fluid bottles 105 preferably comprise standard wide-mouth standard irrigation pour bottles. Preferred irrigation fluid bottles 105 preferably include bottles of polymer construction, preferably formed from a manually deformable (squeezable) plastic. Fluid bottle 105 preferably contains a bulk volume of irrigation fluid 104.

One preferred irrigation fluid suitable for use as fluid 104 preferably comprises a normal saline solution of sodium chloride (NaCl) dissolved in water. Other preferred irrigation fluids preferably include both sterile and non-sterile lactated ringers, balanced salt solutions, tap water, and the like. Upon reading this specification, those with ordinary skill in the art will now appreciate that, under appropriate circumstances, considering such issues as cost, nature of procedure, availability of material in the field, etc., the use of other irrigation fluids, such as, for example, other sterile solutions, buffered solutions, non-sterile solutions, solutions containing pharmacological agents (antibiotics or analgesics), etc., may suffice.

The bulk volume of irrigation fluid 104 contained in fluid bottle 105 is preferably supplied in volumes ranging between about 250 cc and about 2000 cc (at least embodying herein wherein such at least one releasable coupler is structured and arranged to couple with at least one commercial standard wide mouth standard irrigation pour bottle containing the fluid).

Fluid bottle 105 preferably comprises a semi-rigid (but manually deformable) outer wall 122 enclosing a fluid-holding interior cavity 124. The outer wall 122 preferably comprises a narrowed upper-neck portion 126 terminating at an open mouth opening 128 for discharging the fluid contents of the bottle. Upper-neck portion 126 preferably comprises a set of outer helical threads 130 used by the manufacturer to releasably seal mouth opening 128 with a threaded cap (not shown). Releasable coupler 107 of splash shield 102 preferably comprises a set of internal helical threads 132 comprising a size and pitch complementary to outer helical threads 130 of the bottle. Thus, the preferred arrangements of splash shield 102 allow engagement of the device over mouth opening 128, in place of the cap.

Internal helical threads 132 are preferably formed with a size and pitch providing near "universal" thread compatibility within the above-noted bottle range (at least embodying herein at least one threaded coupler structured and arranged to assist threaded coupling of such hollow cylindrical wall to a threaded opening of a bottle containing the fluid). Splash shield 102 is preferably designed to fit wide mouth standard irrigation bottles comprising slightly differing bottle end opening configurations. More specifically, splash shield 102 is preferably designed to fit any of three commercially-available standard wide-mouth standard irrigation pour bottles having an outer neck diameter in the range of about 3.5 centimeters (cm). These preferred products preferably comprise squeezable standard wide-mouth standard irrigation pour bottles from Baxter Healthcare Corporation of Deerfield Ill., Hospira Worldwide Inc. of Lake Forest Ill., and B. Braun Medical Inc. of Allentown Pa. Preferably, threads 132 have thread dimensions compatible with the above-noted products. Threads 132 preferably comprise 1½-6 UNC thread dimension. Threads 132 preferably comprise 1½-6 UNC coarse thread dimension. Splash shield 102 is preferably designed to fit Preferably, threads 132 comprise helical threads with at least two turns, more preferably at least 2½ turns. Less than two turns increases the likelihood of cross threading problems, and is therefore less preferable. More than 2½ turns helps prevent cross threading and improves universal sealing to a variety of different sized bottles.

FIG. 3 shows a bottom view of splash shield 102, according to the preferred embodiment of FIG. 1. Splash shield 102 preferably comprises a curved body 106 preferably comprising a circumferential outer wall 108, as shown. As used herein, the term "circumferential" is not limited to circular shapes, but is defined as a closed curve, of any preferred shape, which is capable of extending around a region containing a target tissue or structure. In a preferred embodiment of the system, outer wall 108 preferably comprises a generally circular shape and substantially uniform outer diameter A of about 1½ inches, as shown.

Figure 4:
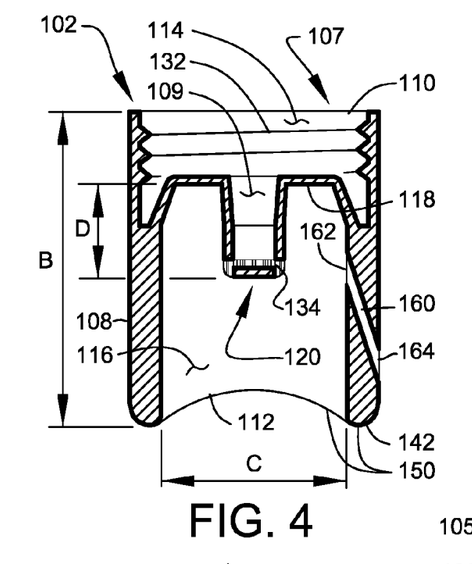
FIG. 4 shows the sectional view 4-4 of FIG. 3 according to the preferred embodiment of FIG. 1.
Figure 5:
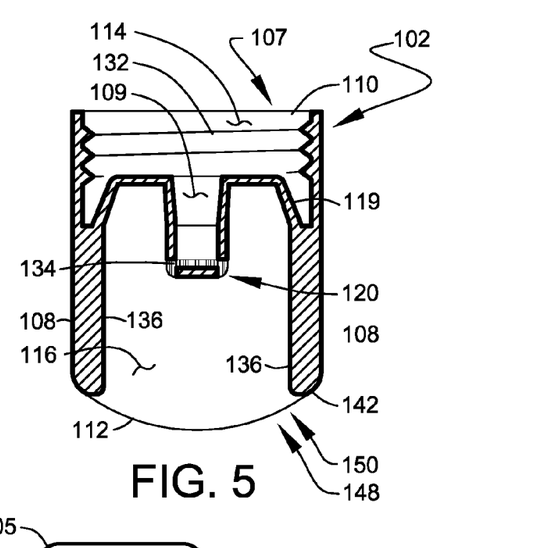
FIG. 5 shows the sectional view 5-5 of FIG. 3 according to the preferred embodiment of FIG. 1.

FIG. 4 shows the sectional view 4-4 of FIG. 3 according to the preferred embodiment of FIG. 1. FIG. 5 shows the sectional view 5-5 of FIG. 3 according to the preferred embodiment of FIG. 1. Reference is now made to FIG. 4 and FIG. 5 with continued reference to FIG. 1 through FIG. 3.

Outer wall 108 preferably comprises an open proximal end 110, an open distal end 112, a proximal interior chamber 114, a distal interior chamber 116, and a transverse dividing wall 118 dividing proximal interior chamber 114 from distal interior chamber 116, as shown. Outer wall 108 comprises a preferred maximum length B of about 2 inches. Distal interior chamber 116 comprises a preferred interior diameter C of about 1 3/16 inch. Upon reading this specification, those with ordinary skill in the art will now appreciate that, under appropriate circumstances, considering such issues as patient age, weight, etc., other size arrangements such as, for example, smaller inner and outer diameters to assist the treatment of pediatric patients, etc., may suffice.

Transverse dividing wall 118 preferably supports at least one sprayer 120, preferably a single cylindrical spray element configured to produce, within distal interior chamber 116, a uniform spray of fluid 104. Sprayer 120 is preferably centered within distal interior chamber 116 and projects outwardly from transverse dividing wall 118 into distal interior chamber 116 a distance D of about 3/4 inch, as shown. The tip of sprayer 120 preferably comprises a radial arrangement of spray apertures 134, preferably about 12 equally-spaced spray apertures 134 configured to discharge fluid 104 in a uniform radial pattern. Interior chamber 114 preferably extends through both transverse dividing wall 118 and the hollow central bore 109 of sprayer 120 to form a conduit-like fluid pathway connecting mouth opening 128 of irrigation fluid bottle 105 to spray apertures 134 (at least embodying herein at least one fluid conduit structured and arranged to conduct the fluid).

Outer wall 108 of distal interior chamber 116 is preferably configured to function as a splash shield, which preferably extends continuously around sprayer 120. Outer wall 108 is thus configured to limit splashing of fluid 104 during production of the spray, greatly reducing the likelihood that an irrigation procedure will contaminate adjacent tissues and surfaces, result in splashing of biological and chemical contaminants onto a health care provider, and/or drench the patient with fluid 104.

Figures 6, 7:
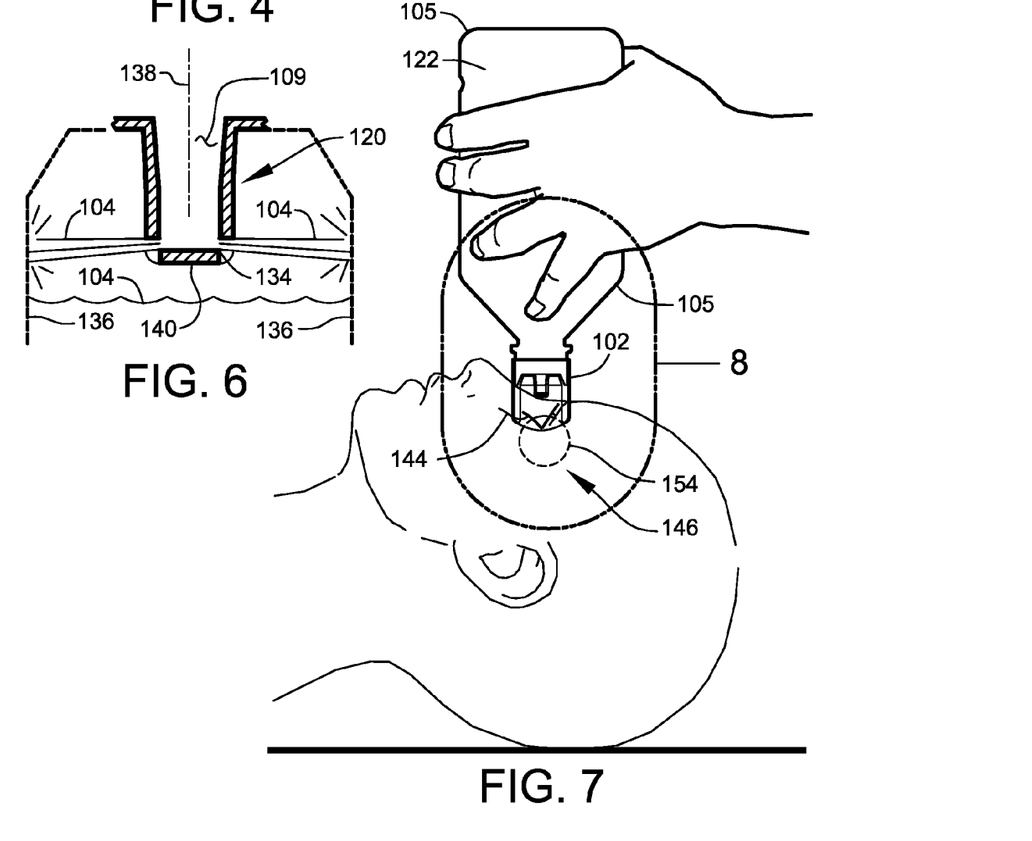
FIG. 6 shows a diagrammatic section view, illustrating a preferred sprayer and preferred orthogonal discharge of the fluid into the splash shield, according to the preferred embodiment of FIG. 1.
FIG. 7 shows a side view illustrating the splash shield and bottle used in an ocular irrigation procedure, according to the preferred embodiment of FIG. 2.
Figure 8:
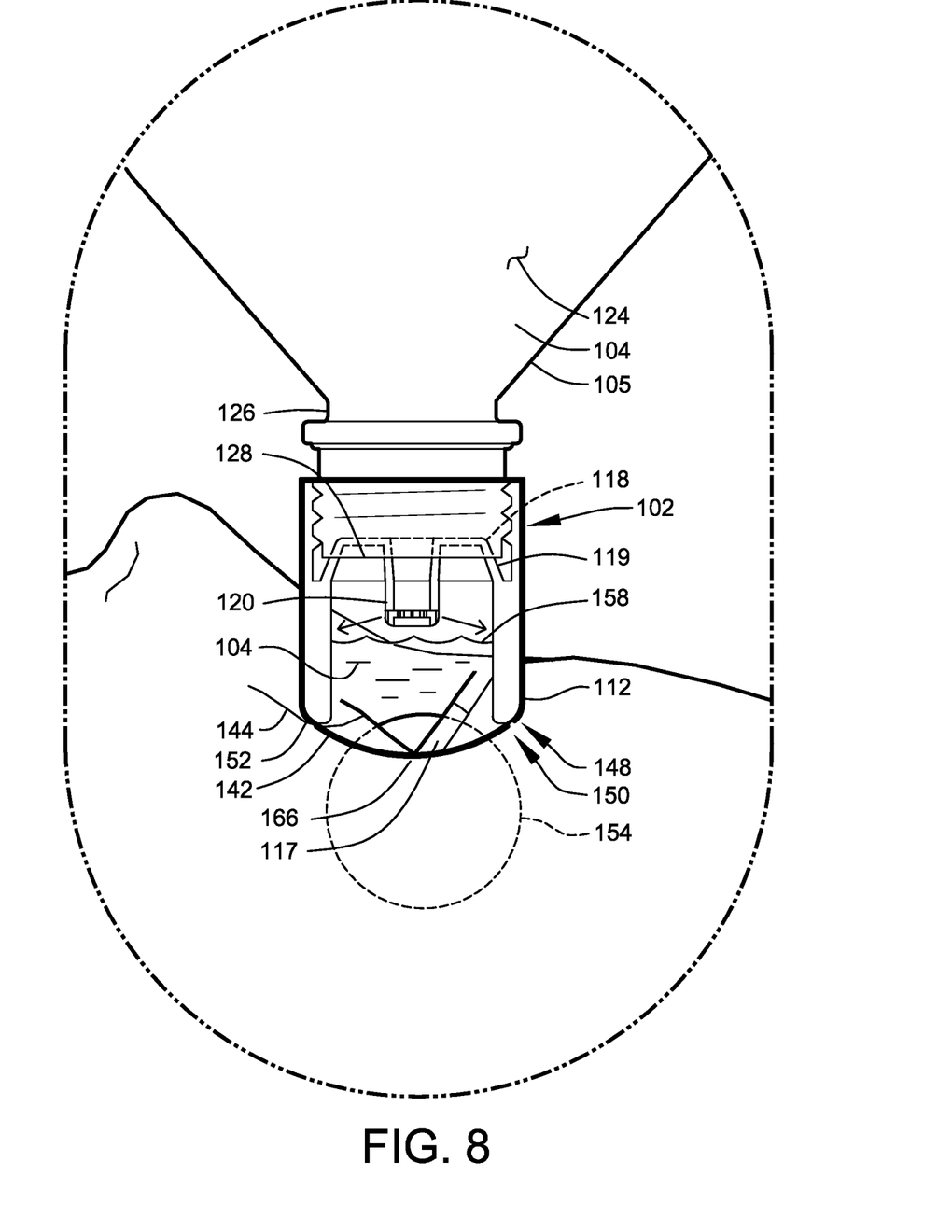
FIG. 8 shows a side detail view, magnified for clarity, of the ocular irrigation procedure of FIG. 7.

FIG. 6 shows a diagrammatic section view, illustrating sprayer 120 and a preferred orthogonal discharge of fluid 104 into distal interior chamber 116. Sprayer 120 is preferably configured to produce at least one diffuse spray of fluid 104 to bathe the target tissues under distal interior chamber 116. Sprayer 120 is preferably configured to direct the radial spray of fluid 104 away from the wound and toward impingement with interior surface 136 of outer wall 108, as shown (at least embodying herein at least one spray director structured and arranged to direct the at least one spray of the fluid generally toward at least one inside surface of such at least one splash shield). More specifically, each spray aperture 134 is circumferentially positioned on the side of sprayer 120, so that fluid 104 exiting the apertures under pressure discharges in a direction generally orthogonal to the central longitudinal axis 138 of sprayer 120, as shown. A solid terminating end wall 140 of sprayer 120 prevents direct spraying of fluid 104 on the wound or other target tissue below open distal end 112. As a result, the preferred structures and arrangements of splash shield 102 are especially useful in assisting clinicians safely irrigate delicate body tissues, preferably including those of the eye, as shown in FIG. 7 and FIG. 8.

FIG. 7 shows a side view illustrating splash shield 102 in a preferred engagement on irrigation fluid bottle 105. The combined unit is shown in use in an ocular irrigation procedure. FIG. 8 shows a side detail view, magnified for clarity, of the ocular irrigation procedure of FIG. 7.

The thickened outer wall 108 of open distal end 112 preferably terminates at smoothly rounded peripheral edges, as shown. The end termination of open distal end 112 preferably forms anatomical engager 142 configured engage the anatomical structures 144 surrounding the target tissue 146 to be treated. Anatomical engager 142 preferably comprises at least one body-conforming shape 148 designed to generally conform open distal end 112 to the surface topography of the anatomical structures 144 surrounding the target tissue 146, as shown.

In the preferred embodiment depicted in FIG. 1 through FIG. 9, anatomical engager 142 preferably comprises a facial engager 150 configured to engage the periorbital facial structures 152 surrounding eye 154, as shown. The preferred shape of facial engager 150 generally resembles a saddle (see FIG. 4 and FIG. 5). Upon reading this specification, those with ordinary skill in the art will now appreciate that, under appropriate circumstances, considering such issues as intended use, user preference, clinical conventions and policies, etc., other anatomical engager arrangements such as, for example, shapes accommodating the ear, shapes accommodating digits of the hand, etc., may suffice.

The preferred shape-conforming arrangements of anatomical engager 142 assists in forming a fluid-retaining seal 151 between open distal end 112 and the periorbital facial structures 152 surrounding eye 154. When open distal end 112 is engaged on the anatomical structures 144 surrounding target tissue 146, a fluid-holding chamber 156 is formed within distal interior chamber 116, a shown. Distal interior chamber 116 is thus preferably able to hold at least one administered volume 158 of fluid 104 in physical contact with eye 154 or other target tissue 146 (at least embodying herein wherein such at least one shape conformer is configured to assist in the formation of at least one fluid-retaining seal between such at least one anatomical engager and the periorbital facial structures surrounding at least one eye to retain the at least one administered volume of the fluid in physical contact with the at least one eye).

The pool of fluid 104 formed within fluid-holding chamber 156 preferably allows a patient to hold their eye 154 open during administration of the fluid 104. Just as swimming underwater does not stimulate a blinking reflex, the preferred means of fluid administration, by pooling the fluid adjacent the eye, preferably inhibits the patient's blinking reflex; therefore, the system permits sustained contact with the eye and deeper penetration under areas that would have been covered by eyelids 117. This is in contrast to conventional direct-contact irrigation techniques that repeatedly stimulate the blinking reflex during a procedure (that is, eyewash stations, showers, direct streams, etc.), which are less effective in providing continuous treatment.

Figures 9, 10, 11, 12:
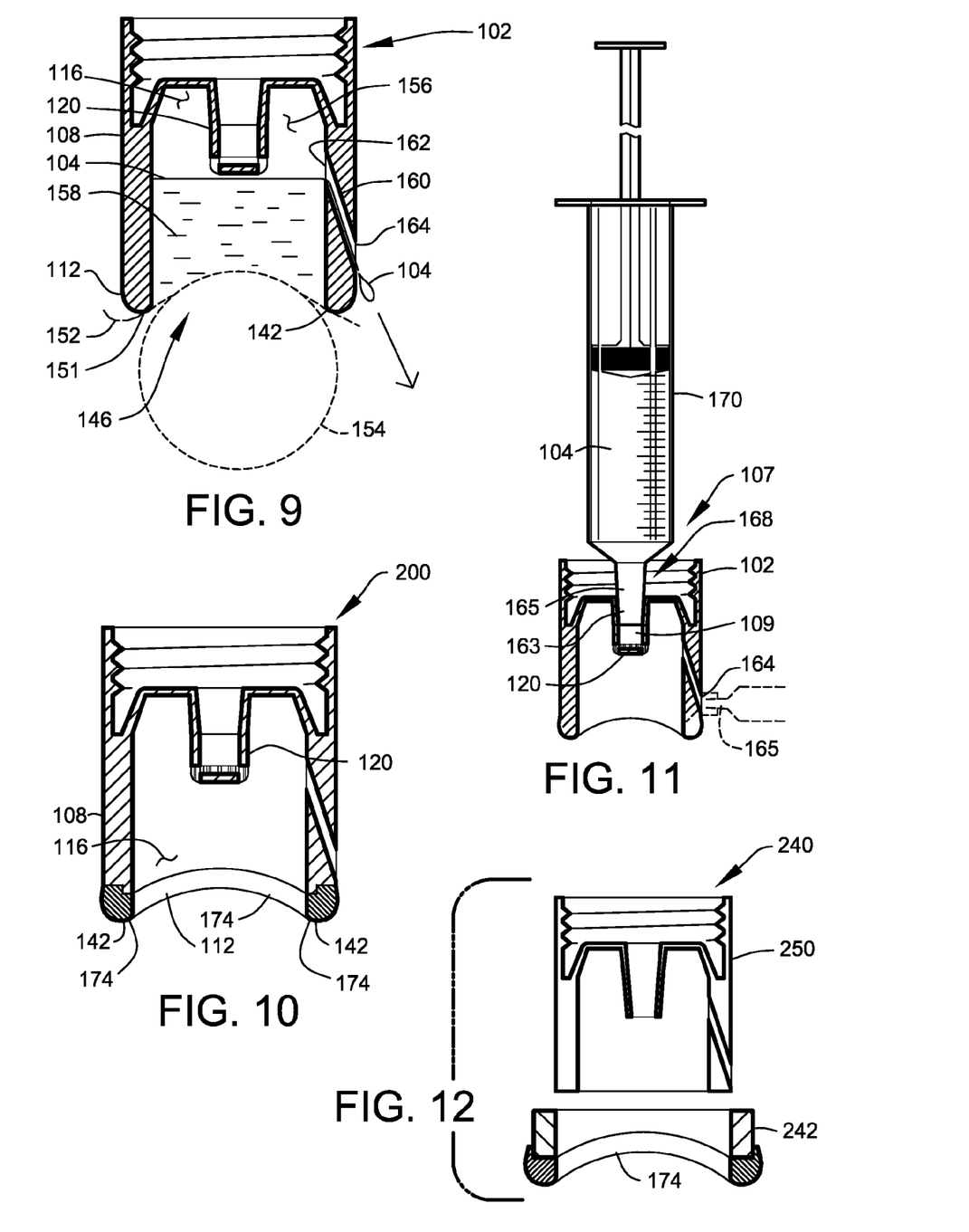
FIG. 9 repeats the sectional view 4-4 of FIG. 3, with the splash shield now shown engaged on periorbital facial structures surrounding the eye of a patient.
FIG. 10 shows a sectional view through the splash shield, illustrating alternate preferred fluid delivery and drainage arrangements, according to the preferred embodiment of FIG. 1.
FIG. 11 shows a sectional view through an alternate splash shield, according to another preferred embodiment of the present invention.
FIG. 12 shows a sectional view through an alternate splash shield assembly, according to another preferred embodiment of the present invention.

FIG. 9 repeats the sectional view 4-4 of FIG. 3, with splash shield 102 shown sealed against the periorbital facial structures 152 surrounding eye 154 of a patient. Distal interior chamber 116 further comprises at least one drainage passage 160, as shown, preferably extending through outer wall 108. Drainage passage 160 is preferably configured to drain excess fluid 104 from within distal interior chamber 116. It is noted that drainage passage 160 also functions as a pressure relief port to maintain a constant (near-ambient) pressure within the chamber during use (to prevent low-pressure suction to eye 154 after the bottle is squeezed).

Drainage passage preferably comprises at least one drainage inlet 162 in fluid communication with the interior of distal interior chamber 116, as shown, and at least one discharge outlet 164 preferably configured to discharge fluid 104 entering drainage inlet 162 to externally of outer wall 108, as shown. As previously noted, drainage passage 160 is preferably configured to retain a minimum administered volume 158 of fluid 104 within the fluid-holding distal interior chamber 116, as shown. Moreover, drainage passage 160 is preferably configured to drain, from distal interior chamber 116, amounts of fluid 104 in excess of the minimum administered volume 158. For eye wounds it is desirable to limit the pressure, but increase the volume of fluid. Accordingly, the preferred embodiments of splash shield system 100 flood a wound or target tissue with a constant but continuously exchanging volume of irrigation fluid 104 delivered from the irrigation fluid source. This preferred arrangement effectively cleanses a wound while protecting fragile tissues from additional trauma that could result from a direct spray of the irrigation fluid on the target tissues.

To maintain the preferred functionality of drainage passage 160 during use, discharge outlet 164 is preferably situated in closer proximity to anatomical engager 142 than drainage inlet 162, as shown. This preferably places discharge outlet 164 below drainage inlet 162 during use, as shown. More specifically, drainage passage 160 passes through outer wall at an angle, wherein the inner drainage inlet 162 comprises a higher vertical elevation than the outer discharge outlet 164 when anatomical engager 142 is oriented in a downward position during use, as depicted in FIG. 7 and FIG. 8.

As shown in the sectional view of FIG. 9, discharge outlet 164 is preferably located within outer wall 108 so as to discharge laterally of the lateral canthus 166 of eye 154 when the saddle-shaped anatomical engager 142 is closely engaged with the periorbital facial structures (at least embodying herein wherein said at least one shape conformer comprises at least one saddle-shaped anatomical engager). This design preference serves to direct excess fluid, discharged from splash shield 102, laterally off the side of the face and away from other anatomical structures of the head.

Releasable coupler 107 is preferably structured and arranged to provide a liquid-tight seal between an irrigation source (e.g., a squeezable wide-mouth irrigation pour bottle) and splash shield 102 so that fluid 104 can escape only through sprayer 120. Releasable coupler 107 preferably utilizes the frustoconical shape of transverse dividing wall 118 to assist in forming such a seal. Preferably, the upper surface of transverse dividing wall 118 comprises a sloping surface 119, as shown. Preferably, sloping surface 119 is structured and arranged to seal against the inner diameter of mouth opening 128, as best illustrated in FIG. 7 and FIG. 8. Sloping surface 119 preferably permits a liquid-tight seal without relying on resilient gaskets or other similar materials. This allows splash shield 102 to be manufactured as one monolithic piece of rigid material to reduce cost. A seal is preferably achieved by screwing splash shield 102 onto irrigation fluid bottle 105 (by threaded engagement of outer helical threads 130 and internal helical threads 132) until mouth opening 128 of the bottle seats on sloping surface 119, as shown in FIG. 7 and FIG. 8. Thus, the up-slanted surface of the preferred apparatus preferably enables sealing on any of the three preferred standard wide mouth standard irrigation pour bottles.

FIG. 10 shows a sectional view through alternate splash shield 200, according to another preferred embodiment of the present invention. Anatomical engager 142 of alternate splash shield 200 preferably comprises a resilient material 174 fitted to open distal end 112, as shown. Resilient material 174 preferably functions to enhance the formation of a fluid-retaining seal, enhance the body-conforming quality of anatomical engager 142, and provides additional comfort to the patient during use.

FIG. 11 shows a sectional view through splash shield 102, illustrating alternate preferred fluid delivery and drainage arrangements, according to the preferred embodiment of FIG. 1.

Preferably, releasable coupler 107 further comprises fluid-connector receiver 168 to receive one or more connectors of the source of fluid 104. Fluid-connector receiver 168 is preferably generated by tapering the interior shape of hollow central bore 109, as shown.

In one preferred embodiment of the system, fluid-connector receiver 168 is configured to couple with a medical syringe 170, as shown. Medical syringe 170 is preferably used to dispense fluid 104 into central bore 109 of sprayer 120. In another preferred embodiment of the system, central bore 109 is configured to receive the specific frustoconical shape of a Luer-type connector 163. In this preferred arrangement, Luer-type connector 163 may comprise the distal hub of medical syringe 170, as shown, or may alternately preferably specifically accommodate engagement with a Luer-type slip connector 165, as shown. Upon reading this specification, those with ordinary skill in the art will now appreciate that, under appropriate circumstances, considering such issues as cost, user preference, etc., the use of other fluid sources having Luer-type connectors such as, for example, flexible I.V. bags, etc., may suffice.

Furthermore, preferred embodiments of discharge outlet 164 may also be configured to accommodate engagement with a Luer-type slip connector 165, as shown. Upon reading this specification, those with ordinary skill in the art will now appreciate that, under appropriate circumstances, considering such issues as intended use, user preference, etc., other syringe receiver arrangements such as, for example, Luer-lock type connectors, tubes, alternate coupler fittings, other devices adapted to the discharging of irrigation fluids, etc., may suffice.

Splash shield 102 is preferably constructed from a biologically inert, non-toxic plastic material. As depicted in FIG. 1, outer wall 108 preferably comprises at least one transparent portion configured to provide a view of the target tissue 146 from outside the wall, even when anatomical engager 142 is engaging the anatomical structures surrounding the target tissue to be treated. More preferably, the entire splash shield 102 unit is constructed from a single transparent plastic material. Most preferably, the entire splash shield 102 (including outer wall 108, sprayer 120, releasable coupler 107, etc.) is constructed as a single monolithically-molded transparent polymer unit.

FIG. 12 shows a sectional view through an alternate splash shield assembly 240, according to another preferred embodiment of the present invention. Alternate splash shield assembly 240 preferably utilizes a resilient anatomical engager 242 designed to be attachable over the open distal end 244 of alternate splash shield unit 250, as shown. Alternate splash shield unit 250 preferably comprises an irrigation device having a single directed nozzle, as shown. It is noted that the configuration and operation of such a device is described in greater detail in applicant's co-pending patent application 61/231,638, incorporated herein by reference for further examples of implementation engineering. Anatomical engager 242 preferably comprises resilient material 174, as shown, which is preferably fitted to the distal end portion of alternate splash shield unit 250. Anatomical engager 242, when joined with alternate splash shield unit 250, preferably functions to improve the fit of the device to the anatomical structures surrounding the target tissue to be treated, enhances the formation of a fluid-retaining seal, and provides additional comfort to the patient during use.

Figures 13, 14:
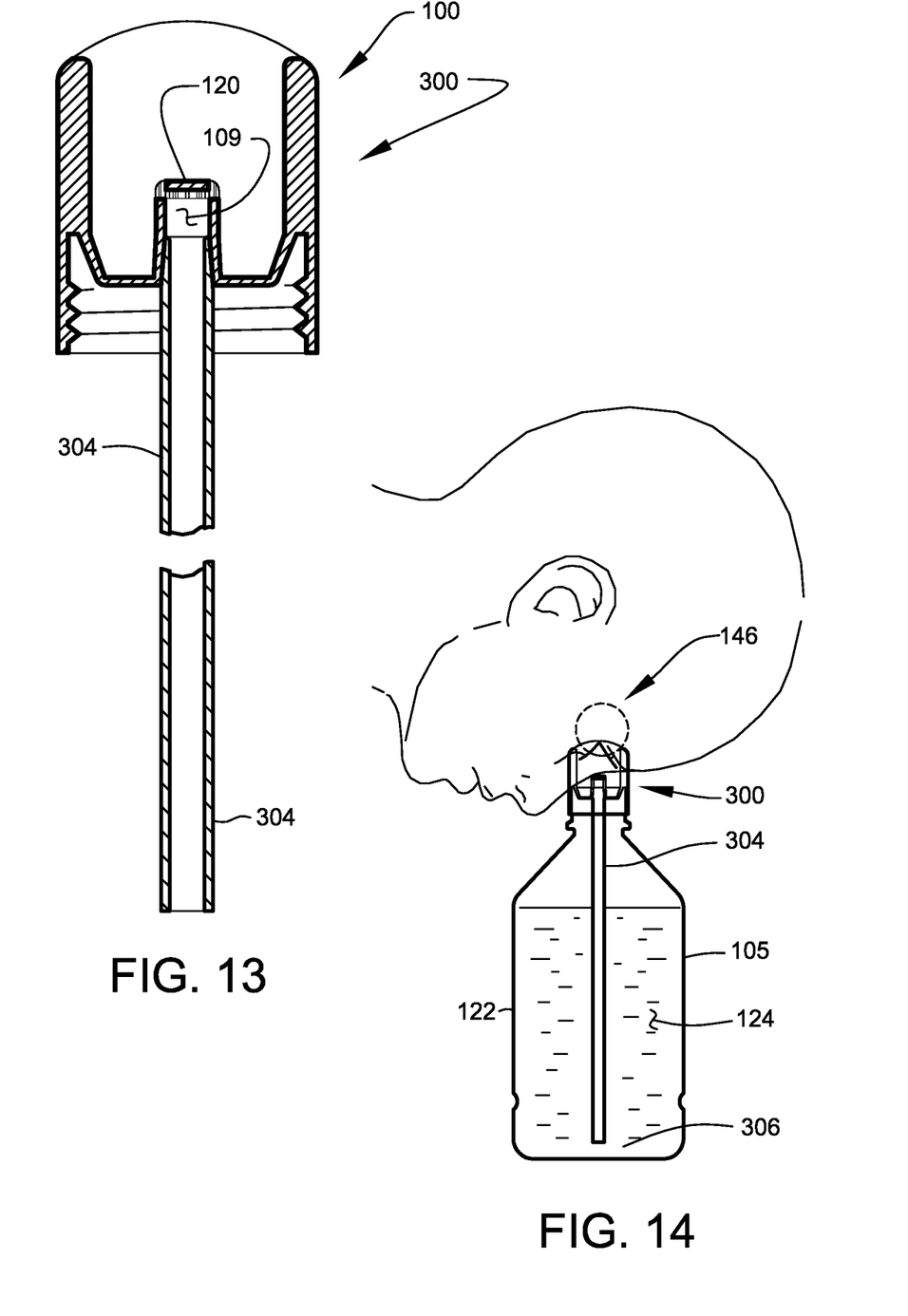
FIG. 13 shows a sectional view through an alternate splash shield assembly, according to another preferred embodiment of the present invention.
FIG. 14 shows a side view illustrating the alternate splash shield used in an inverted ocular irrigation procedure, according to the preferred embodiment of FIG. 13.

FIG. 13 shows a sectional view through alternate splash shield 300, according to another preferred embodiment of the present invention. FIG. 14 shows a side view illustrating alternate splash shield 300 used to perform an inverted ocular irrigation procedure 302, according to the preferred embodiment of FIG. 13. It is noted that alternate splash shield 300 comprises physical arrangements substantially similar to the preferred embodiment of FIG. 1; thus, only the differences between alternate splash shield 300 and the prior embodiment will be elaborated upon.

The preferred structures and arrangements of alternate splash shield 300 enables the irrigation of anatomical target tissues with the tissues positioned generally superior to fluid-holding chamber 156, as shown. The inverted irrigation position depicted in FIG. 14 preferably allows for immersion of target tissues 146 while reducing the likelihood that the irrigation procedure will contaminate adjacent tissues and surfaces and/or drench the patient with fluid 104. This is of significant benefit in ocular irrigation procedures where cross contamination of the unaffected is of concern.

The functioning of alternate splash shield 300 is preferably enabled by inclusion of an elongated fluid conduit 304 to couple the hollow central bore 109 of sprayer 120 to at least one lower internal region 306 of the fluid-holding interior cavity 124 of irrigation fluid bottle 105, as shown. Elongated fluid conduit 304 is preferably designed to convey fluid 104 upwardly to sprayer 120 when pressure within irrigation fluid bottle 105 is increased (above the ambient pressure) by manually squeezing deformable outer wall 122. Target tissues 146 are preferably bathed in a pool of fluid 104 generated in fluid-holding chamber 156 by the transport of fluid 104 upwardly from irrigation fluid bottle 105. Upon reading this specification, those with ordinary skill in the art will now appreciate that, under appropriate circumstances, considering such issues as cost, user preference, etc., other arrangements such as, for example, modifying a sprayer to issue a direct spray to the tissues, utilizing a removable conduit, utilizing conduits of adjustable length, etc., may suffice.

Although applicant has described applicant's preferred embodiments of this invention, it will be understood that the broadest scope of this invention includes modifications such as diverse shapes, sizes, and materials. For example, upon reading this specification, those with ordinary skill in the art will now appreciate that, under appropriate circumstances, considering such issues as intended use, etc., other modifications such as, for example, providing a tube extending from the sprayer bore into the bottle to allow the device to be used in an inverted position, etc., may suffice. Such scope is limited only by the below claims as read in connection with the above specification. Further, many other advantages of applicant's invention will be apparent to those skilled in the art from the above descriptions and the below claims.

What is claimed is:

1. A medical system relating to medical procedures involving fluid irrigation of tissues comprising:
   a) at least one sprayer configured to produce at least one spray of fluid to bathe at least one target tissue;
   b) substantially surrounding said at least one sprayer, at least one splash shield structured and arranged to limit splashing of the fluid during production of the at least one spray; and
   c) at least one fluid conduit structured and arranged to conduct the fluid between at least one source of the fluid and said at least one sprayer;
   d) wherein said at least one sprayer comprises at least one spray director structured and arranged to direct the at least one spray of the fluid generally orthogonally toward impingement with at least one inside surface of said at least one splash shield; and
   e) wherein the fluid is delivered substantially indirectly to the at least one target tissue.

2. The medical system according to claim 1 wherein said at least one splash shield further comprises at least one anatomical engager configured engage at least one anatomical structure surrounding the at least one target tissue during production of the at least one spray.

3. The medical system according to claim 2 wherein said at least one splash shield further comprises at least one fluid retainer configured to retain, when said at least one anatomical engager is engaged with the at least one anatomical structure, at least one administered volume of the fluid in physical contact with the at least one target tissue.

4. The medical system according to claim 3 further comprising at least one releasable coupler structured and arranged to releasably couple said at least one fluid conduit to at least one source of the fluid.

5. The medical system according to claim 3 wherein said at least one releasable coupler comprises at least one threaded coupler structured and arranged to threadably engage at least one bottle-type container containing the fluid.

6. The medical system according to claim 5 wherein said at least one threaded coupler is structured and arranged to couple with at least one standard wide-mouth standard irrigation pour bottle containing the fluid.

7. The medical system according to claim 4 wherein said at least one releasable coupler comprises at least one syringe receiver structured and arranged to receive at least one syringe usable to dispense the fluid into said at least one fluid conduit.

8. The medical system according to claim 7 wherein said at least one syringe receiver is structured and arranged to receive at least one Luer-type connector of the at least one syringe.

9. The medical system according to claim 4 wherein said at least one releasable coupler comprises at least one Luer-type connector receiver structured and arranged to receive at least one Luer-type connector of the at least one source of the fluid.

10. The medical system according to claim 7 further comprising at least one syringe receiver structured and arranged to receive at least one syringe usable to dispense the fluid into said at least one fluid conduit.

11. The medical system according to claim 6 wherein said at least one releasable coupler further comprises at least one fluid seal structured and arranged to form at least one fluid resistant seal between the at least one standard wide-mouth irrigation pour bottle and said at least one releasable coupler.

12. The medical system according to claim 5 wherein said at least one fluid retainer comprises:
   a) at least one outer wall configured to form at least one closed curve continuously surrounding the at least one target tissue;
   b) wherein said at least one outer wall comprises said at least one anatomical engager;
   c) wherein, when engaged on the at least one anatomical structure surrounding the at least one target tissue, said at least one splash shield comprises at least one fluid-holding chamber structured and arranged to hold the at least one administered volume of the fluid in physical contact with the at least one target tissue.

13. The medical system according to claim 12 wherein:
   a) said at least one anatomical engager comprises at least one shape conformer structured and arranged to generally conform to the surface topography of the at least one anatomical structure surrounding the at least one target tissue; and
   b) said at least one shape conformer is configured to assist in the formation of at least one fluid-retaining seal between said at least one anatomical engager and the at least one anatomical structure to retain the at least one administered volume of the fluid in physical contact with the at least one target tissue.

14. The medical system according to claim 12 wherein said at least one anatomical engager comprises at least one resilient material.

15. The medical system according to claim 12 wherein the at least one closed curve of said at least one outer wall comprises at least one substantially circular-shaped section.

16. The medical system according to claim 12 wherein said at least one outer wall further comprises:
   a) extending through said at least one outer wall, at least one drainage passage structured and arranged to drain the fluid from within said at least one fluid-holding chamber;
   b) wherein said at least one drainage passage comprises
      i) in fluid communication with said at least one fluid-holding chamber, at least one drainage inlet, and
      ii) at least one discharge outlet configured to discharge the fluid entering said at least one drainage inlet externally of said at least one outer wall.

17. The medical system according to claim 16 wherein said at least one drainage passage is configured to retain at least one minimum administered volume of the fluid within said at least one fluid-holding chamber and drain, from said at least one fluid-holding chamber, amounts of the fluid in excess of the at least one minimum administered volume.

18. The medical system according to claim 17 wherein:
   a) said at least one discharge outlet is situated in closer proximity to said at least one anatomical engager than said at least one drainage inlet; and
   b) wherein said at least one drainage inlet and said at least one discharge outlet comprise, within said at least one outer wall, differing vertical elevations when said at least one anatomical engager is oriented in a downward contact orientation.

19. The medical system according to claim 1 wherein said at least one splash shield further comprises at least one transparent portion configured to provide a view of the at least one target tissue from outside said at least one splash shield, even when said at least one anatomical engager is engaging the at least one anatomical structure surrounding the at least one target tissue.

20. The medical system according to claim 18 wherein said at least one sprayer, said at least one splash shield and said at least one coupler comprise a single monolithically-molded polymer.

21. The medical system according to claim 18 further comprising:
   a) at least one bottle containing the fluid;
   b) wherein said at least one at least one bottle is operably compatible with said at least one coupler.

22. The medical system according to claim 18 wherein:
   a) said at least one anatomical engager comprises at least one facial engager structured and arranged to engage periorbital facial structures surrounding at least one eye;
   b) said at least one shape conformer is structured and arranged to conform closely to the topography of the periorbital facial structures surrounding at least one eye; and
   c) said at least one shape conformer is configured to assist in the formation of at least one fluid-retaining seal between said at least one anatomical engager and the periorbital facial structures surrounding at least one eye to retain the at least one administered volume of the fluid in physical contact with the at least one eye.

23. The medical system according to claim 22 wherein said at least one shape conformer comprises at least one saddle-shaped anatomical engager.

24. The medical system according to claim 22 wherein said at least one discharge outlet is positioned within said at least one outer wall to discharge laterally of the lateral canthus of the at least one eye when said at least one anatomical engager is engaged to form the at least one fluid-retaining seal with the periorbital facial structures.

25. The medical system according to claim 18 wherein said at least one discharge outlet is sized to receive at least one Luer-type slip connector.

26. A medical system relating to medical procedures involving irrigation of at least one eye comprising:
   a) at least one fluid conduit structured and arranged to conduct the fluid;
   b) in fluid communication with said at least one fluid, wherein said at least one sprayer comprise at least one spray director structured and arranged to direct the at least one spray of the fluid generally orthogonally toward impingement with at least one inside surface of said at least one splash shield, and the fluid is delivered substantially indirectly to the at least one target tissue; conduit
      i) at least one sprayer configured to produce at least one spray of the fluid and
      ii) at least one threaded coupler structured and arranged to threadably couple said at least one sprayer with at least one bottle containing the fluid; and
   c) substantially surrounding said at least one sprayer, at least one splash shield structured and arranged to limit splashing of the fluid during production of the at least one spray of the fluid;
   d) wherein said at least one splash shield comprises at least one facial-engager configured to engage periorbital facial structures surrounding the at least one eye;
   e) wherein said at least one facial-engager comprises at least one shape conformer structured and arranged to conform closely to the topography of the periorbital facial structures surrounding at least one eye; and
   f) wherein said at least one shape conformer is configured to assist in the formation of at least one fluid-retaining seal between said at least one facial-engager and the periorbital facial structures to pool at least one administered volume of the fluid in physical contact with the at least one eye, flooding the at least one eye.

27. The medical system according to claim 26 wherein said at least one splash shield further comprises:
   a) at least one outer wall configured to form at least one closed curve continuously surrounding the at least one eye;
   b) wherein said at least one outer wall comprises said at least one facial-engager; and
   c) wherein, when engaged on the periorbital facial structures surrounding the at least one eye, said at least one splash shield comprises at least one fluid-holding chamber structured and arranged to hold the at least one administered volume of the fluid in physical contact with the at least one eye.

28. The medical system according to claim 26 wherein said at least one facial-engager comprises at least one resilient material.

29. The medical system according to claim 26 wherein said at least one facial-engager comprises a saddle-like shape.

30. The medical system according to claim 29 wherein said at least one facial-engager is removeably attachable with said at least one outer wall.

31. The medical system according to claim 26 wherein said at least one coupler comprises at least one threaded coupler structured and arranged to threadably engage at least one bottle-type container containing the fluid.

32. The medical system according to claim 26 wherein said at least one releasable coupler further comprises at least one syringe receiver structured and arranged to receive at least one syringe usable to dispense the fluid into said at least one fluid conduit.

33. The medical system according to claim 27 wherein said at least one outer wall further comprises:
   a) extending through said at least one outer wall, at least one drainage passage structured and arranged to drain the fluid from within said at least one fluid-holding chamber;
   b) wherein said at least one drainage passage comprises
      i) in fluid communication with said at least one fluid-holding chamber, at least one drainage inlet, and
      ii) at least one discharge outlet configured to discharge the fluid entering said at least one drainage inlet externally of said at least one outer wall.

34. The medical system according to claim 33 wherein said at least one drainage passage is configured to retain at least one minimum administered volume of the fluid within said at least one fluid-holding chamber and drain, from said at least one fluid-holding chamber, amounts of the fluid in excess of the at least one minimum administered volume.

35. The medical system according to claim 33 wherein:
   a) said at least one discharge outlet is situated in closer proximity to said at least one facial-engager than said at least one drainage inlet; and
   b) wherein said at least one drainage inlet and said at least one discharge outlet comprise, within said at least one outer wall, differing vertical elevations when said at least one facial-engager is oriented in a downward contact with the periorbital facial structures.

36. The medical system according to claim 26 wherein said at least one splash shield further comprises at least one transparent portion configured to provide a view of the at least one target tissue from outside said at least one splash shield, even when said at least one facial-engager is engaging the periorbital facial structures surrounding the at least one eye.

37. The medical system according to claim 36 wherein said at least one sprayer, said at least one splash shield and said at least one releasable coupler comprise a single monolithically-molded polymer.

38. The medical system according to claim 31 further comprising:
   a) at least one bottle containing the fluid;
   b) wherein said at least one at least one bottle is operably compatible with said at least one coupler.

39. The medical system according to claim 38 wherein said at least one discharge outlet is sized to receive at least one Luer-type slip connector.

40. The medical system according to claim 38 further comprising extending into said at least one at least one bottle, at least one fluid transport tube configured to transport the fluid from a bottom portion of said at least one at least one bottle to said at least one fluid conduit.

41. A medical system relating to ophthalmologic medical procedures involving fluid irrigation of at least one eye, said system comprising:
   a) a hollow cylindrical wall comprising an open proximal end, an open distal end, a proximal interior chamber, a distal interior chamber, and a transverse dividing wall to transversely divide said proximal interior chamber from said distal interior chamber;
   b) wherein said open distal end comprises a threaded coupler structured and arranged to assist threaded coupling of said hollow cylindrical wall to a threaded opening of a bottle containing the fluid;
   c) wherein said transverse dividing wall comprises, at least one sprayer configured to produce, within said distal interior chamber, at least one directed spray of the fluid discharged into said proximal interior chamber from the bottle containing the fluid;
   d) wherein said open distal end comprises at least one facial-engager configured to engage periorbital facial structures of the at least one eye; and
   e) wherein the at least one directed spray of the fluid by said at least one sprayer is configured to direct the at least one spray of the fluid orthogonally toward impingement with an interior surface of said hollow cylindrical wall of said distal interior chamber.

42. The medical system according to claim 41 wherein said a distal interior chamber is structured and arranged to hold a pool of the fluid, discharged from said at least one sprayer, in contact with the at least one eye.

43. A medical system relating to medical procedures involving fluid irrigation of tissues comprising:
   a) at least one sprayer configured to orthogonally produce at least one spray of fluid to bathe at least one target tissue;
   b) substantially surrounding said at least one sprayer, at least one splash shield structured and arranged to limit splashing of the fluid during production of the at least one spray;
   c) at least one releasable coupler structured and arranged to couple with at least one bottle-type container containing the fluid; and
   d) at least one fluid conduit structured and arranged to conduct the fluid between the at least one bottle-type container containing the fluid and said at least one sprayer;
   e) wherein said at least one splash shield comprises at least one anatomical engager structured and arranged to engage at least one anatomical structure surrounding the at least one target tissue during production of the at least one spray; and
   f) wherein said at least one anatomical engager comprises a saddle-like shape.

44. The medical system according to claim 43 wherein said at least one anatomical engager is removeably attachable to said at least one splash shield.

* * * * *

UNITED STATES PATENT AND TRADEMARK OFFICE
CERTIFICATE OF CORRECTION

PATENT NO. : 8,672,904 B1
APPLICATION NO. : 12/714316
DATED : March 18, 2014
INVENTOR(S) : Joseph P. Schultz It is certified that error appears in the above-identified patent and that said Letters Patent is hereby corrected as shown below:

In the Claims:

Column 17, Claim 38 b), line 48, reads: "wherein said at least one at least one bottle is"
--which should read: "wherein said at least one bottle is"

Column 17, Claim 40, line 54, reads: "extending into said at least one at least one bottle, at"
--which should read: "extending into said at least one bottle, at"

Column 17, Claim 40, line 56, reads: "portion of said at least one at least one bottle to"
--which should read: "portion of said at least one bottle to"

Signed and Sealed this
Tenth Day of June, 2014

Michelle K. Lee
*Deputy Director of the United States Patent and Trademark Office*